United States Patent [19]
Tangherlini et al.

[11] Patent Number: 5,651,771
[45] Date of Patent: Jul. 29, 1997

[54] ADJUSTABLE SURGICAL CLAMP

[75] Inventors: Vincent C. Tangherlini, Rancho Santa Margarita; Martin V. Shabaz, Santa Ana, both of Calif.

[73] Assignee: Applied Medical Resources Corporation, Laguna Hills, Calif.

[21] Appl. No.: 335,056

[22] Filed: Nov. 7, 1994

[51] Int. Cl.⁶ .................................................. A61M 25/00
[52] U.S. Cl. ...................... 604/158; 604/165; 604/280; 604/283
[58] Field of Search .................... 604/158, 161, 604/164, 165, 264, 280, 283, 171, 174

[56] References Cited

U.S. PATENT DOCUMENTS

| | | | |
|---|---|---|---|
| 5,242,427 | 9/1993 | Bilweis | 604/264 |
| 5,300,046 | 4/1994 | Scarfone et al. | 604/264 |
| 5,334,157 | 8/1994 | Klein et al. | 604/160 |
| 5,370,625 | 12/1994 | Shichman | 604/165 X |
| 5,391,152 | 2/1995 | Patterson | 604/280 X |

*Primary Examiner*—John D. Yasko
*Attorney, Agent, or Firm*—Richard L. Myers

[57] ABSTRACT

An adjustable surgical clamp having an axis that is adapted to releasably engage the outer surface of a cylindrical instrument such as a trocar. An elastomeric sleeve has an outer surface and an inner surface which is sized to frictionally engage the instrument. A constriction member forming a ring around the sleeve is operable between a first position wherein the ring has a first diameter and a second position wherein the ring has a second diameter. A pair of tabs attached to the constriction member are movable relative to each other to operate the constriction member between the first and second positions. A tube extending axially of the constriction member includes a protrusion which may be in the form of a helix, a plurality of annuli or an inflatable balloon enhances the fixed relationship with a body wall.

21 Claims, 4 Drawing Sheets

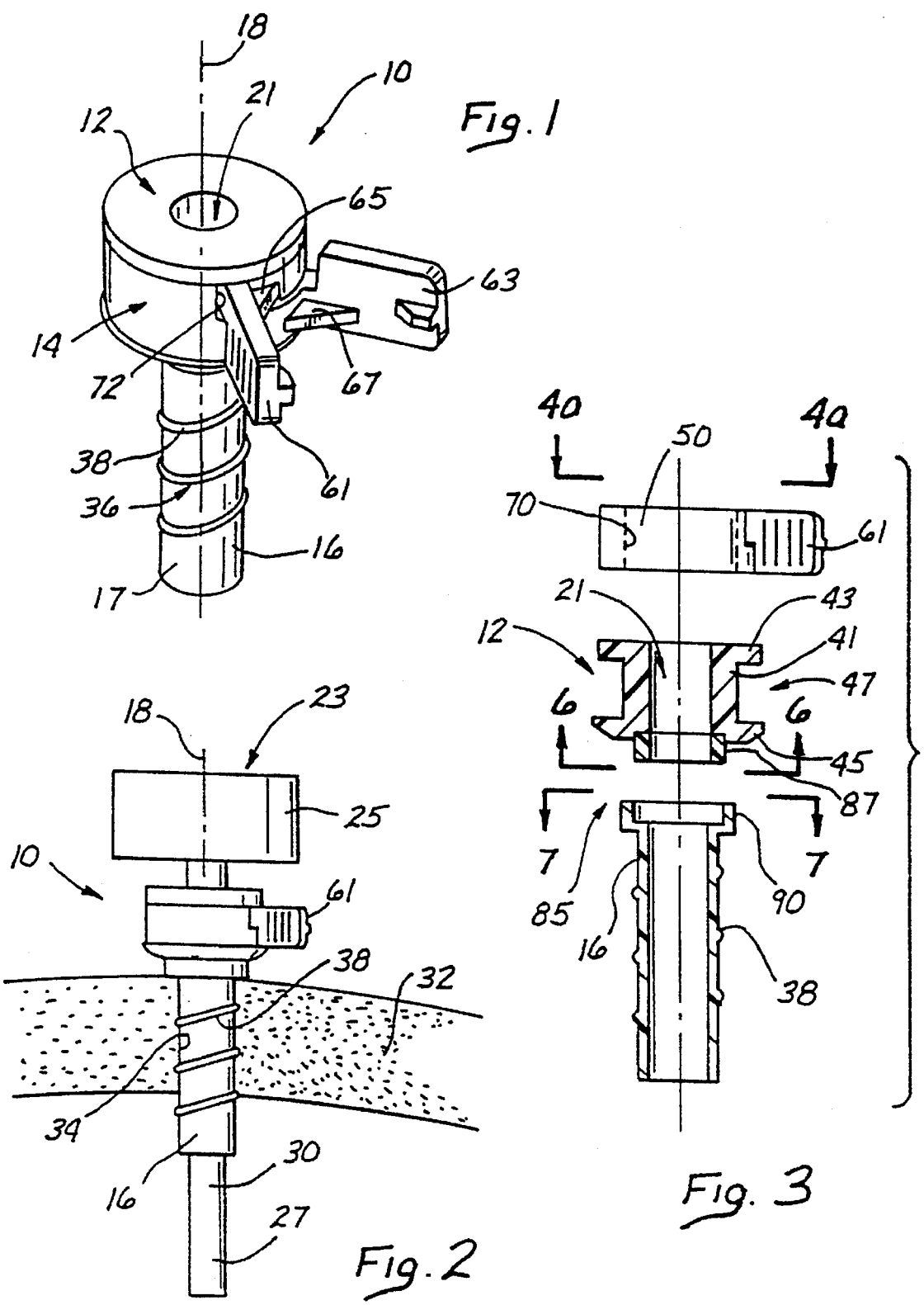

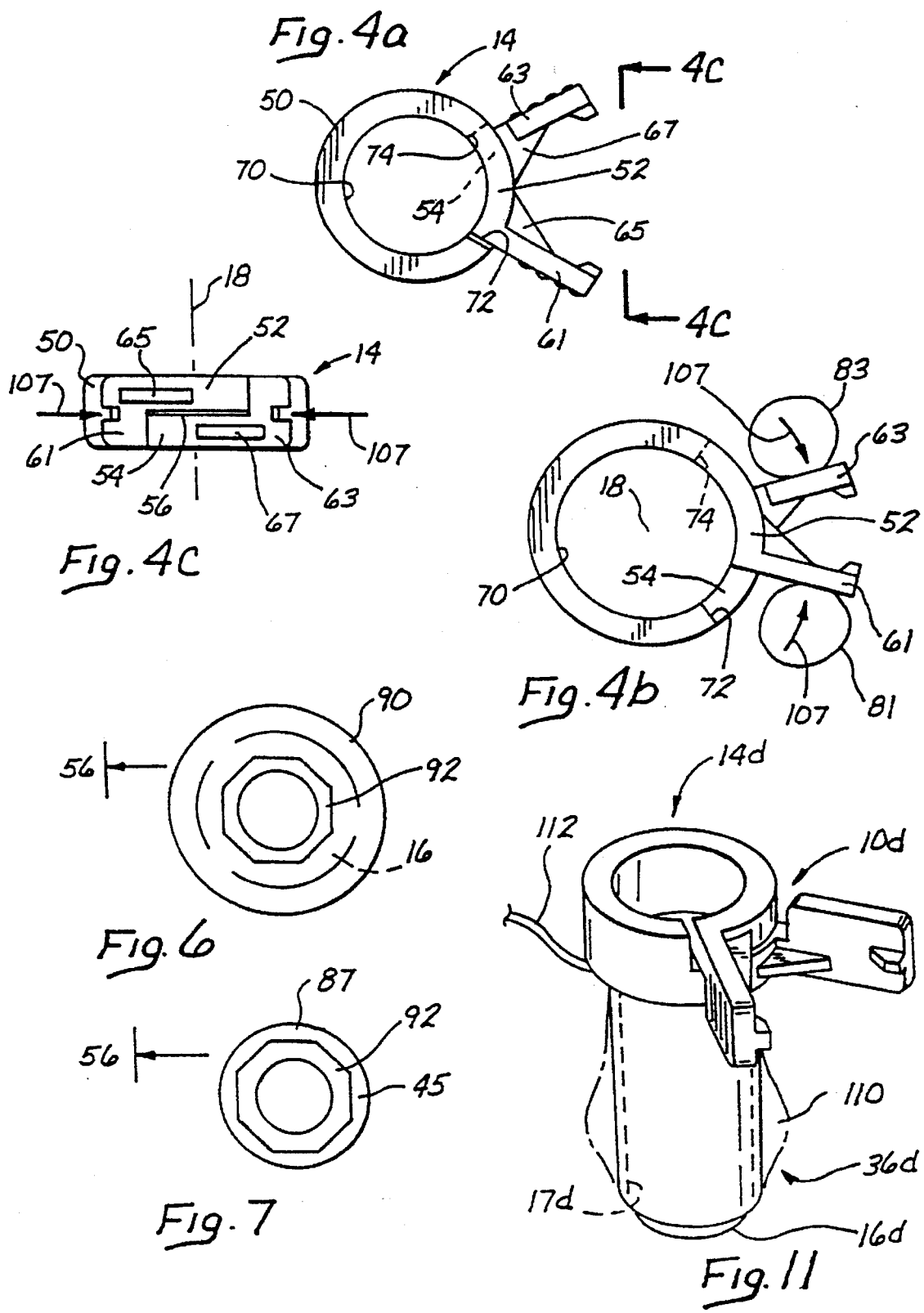

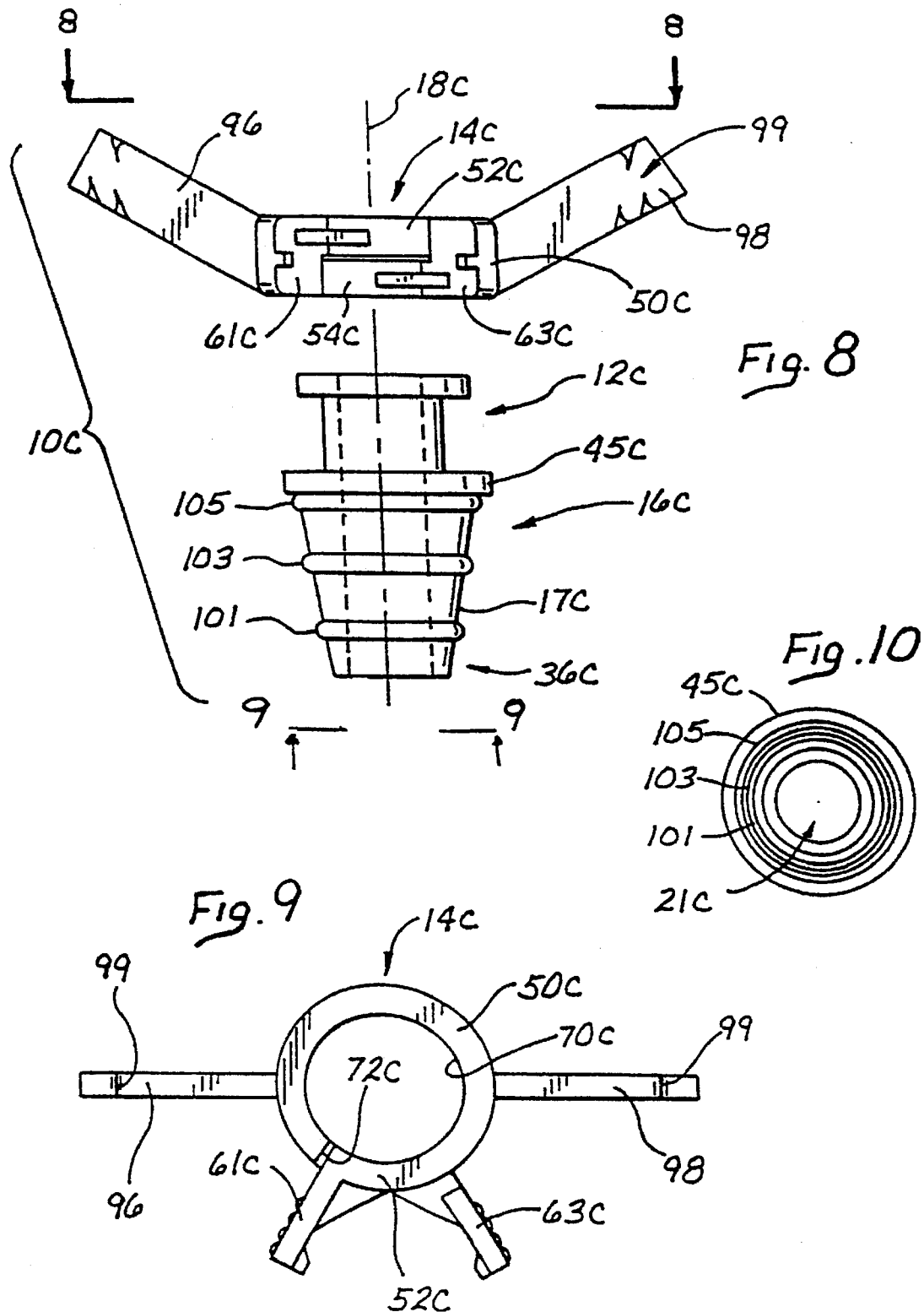

ADJUSTABLE SURGICAL CLAMP

BACKGROUND OF THE INVENTION

1. Field of the Invention

This invention relates generally to surgical clamps and more specifically to clamps which adjustably engage and hold surgical instruments in a generally fixed relationship with a body structure such as a body wall.

2. Discussion of the Prior Art

In the past it has been desirable to hold surgical instruments, such as trocars, in a generally fixed relationship with body structures, such as the abdominal wall. In order to provide for an adjustable relationship between the trocar and the abdominal wall, the clamp has been generally fixed to the abdominal wall but adjustable with respect to the trocar.

The adjustable relationship between the clamp and trocar has been facilitated by a clamp having an elastomeric sleeve sized to receive the trocar in a frictional relationship. A constricting device such as an adjustable collar has been positioned around the sleeve to constrict the sleeve around the trocar. A screw has been provided to tighten the collar and thereby enhance the frictional relationship between the sleeve and trocar. The same screw has been adjustable to relieve the frictional relationship between the sleeve and the trocar thereby permitting the trocar to be maneuvered relative to the body wall.

The prior art also includes adjustable collars which are adjustable in diameter by operation of a circumferential lever between a locked position and a released position. In order to facilitate a generally fixed relationship between the clamp and the abdominal wall, an extension tube has been provided axially of the sleeve and collar. These extension tubes have been formed with helical projections which not only facilitate operative placement of the clamp but also enhance the generally fixed relationship between the clamp and abdominal wall.

In these devices of the prior art, the clamp must be held in one hand in order to operate either the adjustment screw or the lever with the other hand. As a consequence, the simple adjustment of the trocar relative to the body wall has required full attention to operation of the clamp. While other surgical steps and procedures jealously compete for the surgeon's time and attention, the complex structures associated with the clamps of the prior art has demanded that both hands be used in order to adjust the clamp. The structures of the past also involve several parts which must be separately manufactured and assembled to provide the finished clamp. This of course has increased the cost of the product.

SUMMARY OF THE INVENTION

These deficiencies of the prior art are overcome with the present invention which includes an elastomeric sleeve for receiving the surgical instrument, such as a trocar, and a surrounding collar which is operable using a single hand. In a preferred embodiment, the collar includes a base wall and at least one wing which is integral with the base wall and forms the circumferential collar with the base wall. The wing is movable relative to the base wall to constrict or expand the opening formed by the collar around the sleeve. First and second tabs are provided that are movable relative to each other along a path of movement, the first tab has a fixed relationship with the base wall, while the second tab is integral with the wing. The tabs are biased to a generally separated relationship which is associated with the reduced diameter of the collar. When the tabs are moved relative to each other, the collar expands to reduce the friction of the sleeve against the trocar. By merely holding the tabs between the thumb and first finger, the clamp can be fully operated using a single hand. Not only can the clamp be released from frictional engagement with the trocar, but the clamp can also be maneuvered relative to the body wall using only two fingers.

It is of particular advantage that the collar is biased to the reduced diameter. This enables the collar to automatically grip the trocar by merely releasing the tabs. No separate force is required to operate a screw or lever in order to achieve this frictional engagement of the trocar. In a particular embodiment, the tube which engages the abdominal wall is attached to the sleeve by way of a connector having a first portion and a second portion. The first portion of the connector is molded into the elastomeric sleeve while the second portion of the connector is formed as part of the tube. A snap fit relationship facilitates easy assembly of these components.

In a particular embodiment, the tube can be formed with an exterior balloon which is inflatable to anchor the tube and clamp relative to the abdominal wall and also to exert tamponade pressure on the abdominal wall at the puncture site. While the wall engaging tube can be provided with a helical projection on a generally cylindrical surface, the invention can also be embodied with a tube having a conical outer surface and projections in the form of axially spaced annuli.

In one aspect of the invention, a combination is disclosed for accessing a body cavity through a body wall. A trocar including a cannula having an axis and an outer surface is adapted to extend through the body wall to provide a working channel into the body cavity. A laparoscopic clamp is operable to releasibly engage the cannula and is maneuverable to an operative position relative to the body wall in order to provide the cannula and the body wall with a generally fixed relationship. The clamp includes an elastomeric sleeve which is actuable between a first position wherein the sleeve has a fixed relationship with the cannula, and a second position wherein the sleeve has a sliding relationship with the cannula. An actuation collar is included in the clamp and operable by only one hand of the user to actuate the sleeve between the first and second position in order to adjust the position of the clamp relative to the cannula.

In another aspect of the invention, a surgical clamp having an axis is adapted to releasibly engage the outer surface of a cylindrical instrument. An elastomeric sleeve having an outer surface and an inner surface is sized to frictionally engage the outer surface of the instrument. A constriction member forms a ring around the sleeve and is operable between a first position wherein the ring has a first diameter and a second position wherein the ring has a second diameter larger than the first diameter. A pair of tabs attached to the constriction member are movable relative to each other to operate the constriction member between the first and second positions. A tube extending axially of the constriction member includes a protrusion which enhances the fixed relationship with the body wall. The protrusion can be in the form of a helix, a plurality of annuli, or an inflatable balloon. The tabs are generally movable in a plane which can be either transverse or parallel to the axis of the surgical clamp.

These and other features and advantages of the invention will become more apparent with a discussion of preferred embodiments of the apparatus and method, and reference to the associated drawing.

DESCRIPTION OF THE DRAWINGS

FIG. 1 is a perspective view of one embodiment of the adjustable surgical clamp of the present invention;

FIG. 2 is a side elevation view of the clamp of FIG. 1, operatively disposed to hold a trocar in an adjustably fixed relationship with a body wall;

FIG. 3 is an exploded view of the clamp illustrated in FIG. 1;

FIG. 4a is a top plan view taken along lines 4a—4a of FIG. 3 and illustrating an adjustable collar of the clamp in a contracted state;

FIG. 4b is a top plan view of the adjustable collar of FIG. 4a but illustrating the collar in an expanded state;

FIG. 4c is a side elevation view of the collar taken along the lines 4c—4c of FIG. 4a;

FIG. 5b is a side elevation view of the embodiment illustrated in FIG. 5a;

FIG. 6 is a bottom plan view of an elastomeric sleeve taken along lines 5—5 of FIG. 3;

FIG. 7 is a top plan view of an extension tube of the clamp taken along lines 7—7 of FIG. 3;

FIG. 8 is an exploded view of a further embodiment of the adjustable clamp of the present invention;

FIG. 9 is a top plan view of an adjustable collar having suture flanges and taken along lines 8—8 of FIG. 7;

FIG. 10 is a bottom plan view of a further embodiment of the extension tube taken along lines 9—9 of FIG. 7;

FIG. 11 is a perspective view of a further embodiment of the adjustable clamp of the present invention illustrating an extension tube with an exterior balloon.

DESCRIPTION OF PREFERRED EMBODIMENTS AND BEST MODE OF THE INVENTION

Figure 5A:
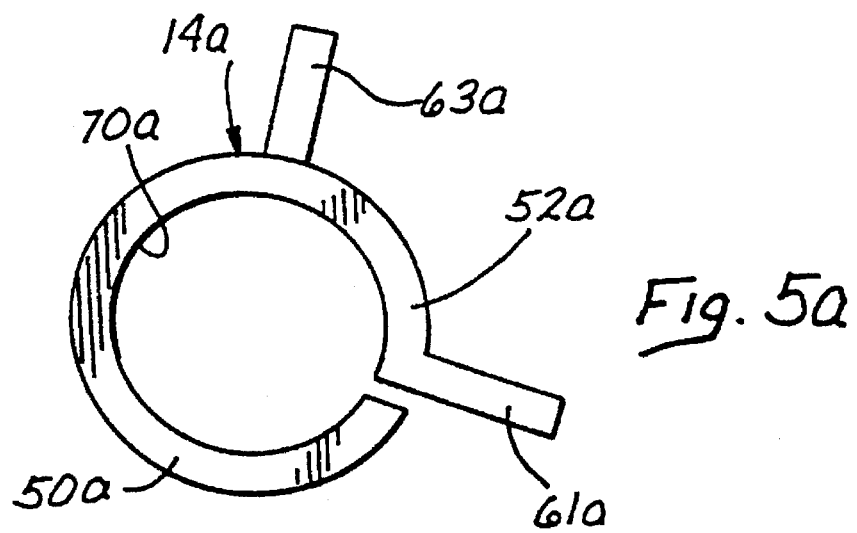
FIG. 5a is a top plan view of an additional embodiment of the surgical clamp of the present invention.

An adjustable surgical clamp is illustrated in FIG. 1 and designated generally by the reference numeral 10. The clamp includes an elastomeric sleeve 12, an adjustable surrounding collar 14 and an extension tube 16 having an outer surface 17, all of which are disposed generally along a common axis 18.

The sleeve 12 and tube 16 define a channel 21 which is sized and configured to receive a surgical instrument such as a trocar 23 illustrated in FIG. 2. The trocar 23 commonly includes a seal housing 25 and a tubular cannula 27 having an outer surface 30. The trocar 23 functions to define a working channel through the cannula 27 in order to provide access through a body wall, such as the abdominal wall 32. It is the purpose of the clamp 10 to hold the trocar 23 in a relationship to the wall 32 which is generally fixed along the axis 18.

Part of this function is served by the extension tube 16 which maintains a generally fixed, typically perpendicular, relationship with the wall 32. Initially, a puncture site 34 is created in the wall 32 using an obturator (not shown). The extension tube 16 is inserted into this puncture site 34 when projections 36 along the tube 16 aid in maintaining the tube 16 and the wall 32 in a fixed relationship. In the illustrated embodiment, the projections 36 take the form of a helix 38 which also facilitates insertion of the tube 16 into the puncture site 34. With the projections 36 in a helical configuration, the tube 16 can be screwed into the wall 32 at the site 34.

One of the primary functions of the clamp 10 is to maintain the trocar 23 in a generally fixed axial relationship with the clamp 10, and hence a generally fixed relationship with the wall 32. This preferred fixed relationship may vary with the preference with the surgeon as well as the particular operation being undertaken. For this reason, the clamp 10 is momentarily adjustable to permit axial movement between the trocar 23 and the elastomeric sleeve 12. When the desired fixed relationship between the trocar 23 and the sleeve 12 is achieved, the clamp is tightened to maintained the desired position in a fixed relationship. This ability to adjust the relationship between the clamp 10 and the trocar 23 among a multiplicity of fixed positions is a principle feature of the present invention.

Referring to the axial cross section view of FIG. 3, it can be seen that the sleeve 12 includes a central wall 41 extending between a pair of annular flanges 43 and 45 which are disposed at opposite ends of the wall 41. While the central wall 41 defines the inner channel 21, the flanges 43 and 45 define an outer annular recess 47. It is this recess 47 into which the collar 14 fits to radially compress the sleeve 12 in order to vary the diameter of the channel 21.

Operation of the collar 14 can best be understood with reference to FIGS. 4a, 4b and 4c. In these views, the collar 14 is illustrated to include a base 50 and a pair of wings 52 and 54 which are axially spaced to define a slot 56. A pair of finger tabs 61 and 63 are attached to the respective wings 52, 54 and reinforced by flanges 65 and 67 respectively. In the illustrated embodiment, the base 50 and wings 52, 54 collectively define an inner circumference 70 of the collar 14. It is this inner circumference 70 which is disposed in contact with the central wall 41 of the sleeve 12.

Although the slot 56 separating the wings 52 and 54 in the illustrated embodiment is generally perpendicular to the axis 18, this is not required by the invention. Generally the slot can have any transverse orientation relative to the axis 18 as long as the wings 52, 54 remain in a connected, typically integral, relationship with the base 50 of the collar 14.

At these points of connection between the wings 52, 54 and the base 50, a shoulder is formed to define each end of the base 50. For example, where the wing 52 connects to the base 50, a shoulder 72 is formed at one end of the base 50. At the opposite end of the base 50, a shoulder 74 is formed where the wing 52 is connected to the base 50. These shoulders 72 and 74 define axial recesses which are sized to receive the opposing wing 52, 54. With this relationship, the base 50 and wings 52, 54 provide the collar 14 in a preferred embodiment with a cylindrical configuration and a substantially constant axial dimension.

In this embodiment of FIGS. 1–4, the tabs 61, 63 are attached to the ends of the associated wings 52, 54. This preferred location provides the greatest leverage and spacing for the tabs 61, 63 in a preferred embodiment. With reference to FIG. 4a it will be apparent that the shoulders 72, 74 can be placed in close proximity to the respective tabs 61, 63. This relationship is not required by the invention. However, it will be noted that the angular length of the base 50 relative to the wings 52, 54 has an effect on the adjustability of the collar 14 as described in greater detail below. In general, the longer the wings 52, 54 relative to the base 50, the greater the ease of adjustment. However, ease of adjustment is typically accompanied by a reduced frictional force between the sleeve 12 and trocar 23 which can adversely affect their desired fixed relationship as discussed with reference to FIG. 2.

The collar 14 is typically formed from a plastic material which is molded to a natural shape defining the inner circumference 70 with a relatively small diameter. However, the plastic material can be bent slightly by application of forces to the wings 52, 54 in order to expand the inner circumference 70 to a relatively large diameter as illustrated in FIG. 4b. In a preferred embodiment, this force is applied by squeezing the tabs 61, 63 into proximity, typically between a thumb 81 and first finger 83, illustrated schematically in FIG. 4b. As the tabs 61, 63 are squeezed into proximity, the base 50, but primarily the wings 52, 54 bend radially away from the axis 18 to expand the inner circumference 70. As the inner circumference 70 of the collar 14 expands, pressure of the collar 14 against the central wall 41 of the sleeve 12 is relieved so that the channel 21 also expands in diameter.

It is important to note that in the preferred embodiment, the base 50 and wings 52, 54 of the collar 14 are biased to a reduced diameter while the central wall 41 of the elastomeric sleeve 12 is biased to an enlarged diameter. With these relationships, operation of the tabs 61 and 63 automatically expands the channel 21 of the sleeve 12 facilitating movement between the trocar 23 and clamp 10. When the tabs 61 and 63 are released in favor of the bias of the collar 14, the central wall 41 is compressed against the bias of the sleeve 12. This compression of the sleeve 12 increases the friction of the sleeve 12 on the outer surface 30 of the cannula 27 in order to maintain the desired fixed relationship between the trocar 23 and clamp 10.

The surfaces of the tabs 61 and 63 which face away from the opposing tabs 61, 63 are roughened by serrations which enhance the frictional relationship with the associated thumb 81 and finger 83. This structural feature enhances the single handed operation which is of particular advantage to the present invention. By facilitating the grip of the finger 81 and thumb 83 on the tabs 61 and 63, respectively, expansion and contraction of the collar 14 can be accomplished using only a single hand. Furthermore, while the tabs 61, 63 are being operated, the entire clamp 10 can be maneuvered by the same thumb 81 and finger 83. No separate hand is required to hold the collar 14 while operating the tabs 61, 63, or to hold the collar 14 in order to maneuver the clamp 10.

The single-hand operation is further enhanced by the fact that the tabs 61, 63 can be moved along a path of movement best illustrated by the arrows 107 in FIG. 4c. In this particular embodiment, the path of movement and the arrows 107 are disposed in a single plane which is transverse (perpendicular in the illustrated embodiment) to the axis 18. Thus, even when the tabs 61, 63 are being moved along the arrows 107, the clamp 10 can be maneuvered to slide the clamp 14 along the cannula 27 of the trocar 23 or move the clamp within the abdominal wall 32.

In further embodiments of the invention, structural elements which are similar to those previously discussed are designated with the same reference numeral followed by a lower case letter. Thus, with reference to FIG. 5a it will be appreciated that a clamp 14a can be formed with only a single wing 52a.

In such an embodiment, the associated tab 61 can be positioned at the end of the wing 54a, but the opposing tab 63a is positioned on the base 50a. In such an embodiment, squeezing the tabs 61a, 63a into proximity expands the single wing 52a to enlarge the inner circumference 70a of the collar 14a.

Figure 5B:
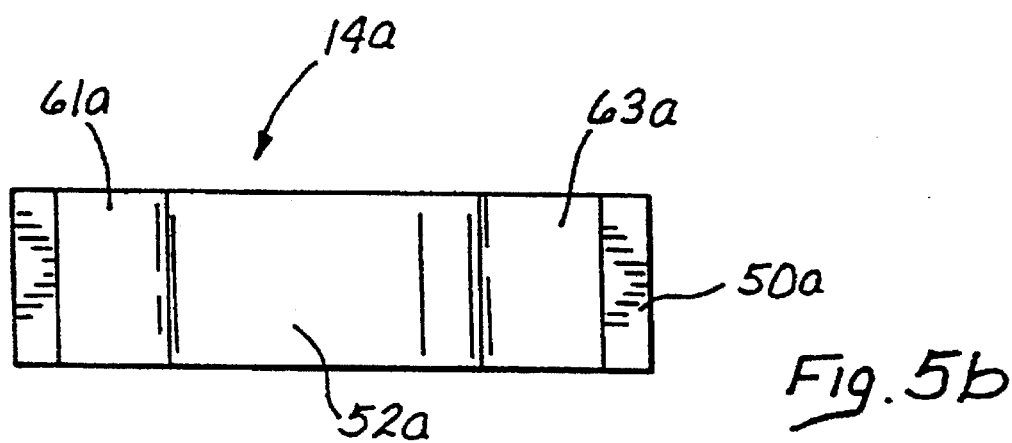

Understanding the simplified construction of the embodiment illustrated in FIG. 5a and 5b helps one appreciate that in the embodiment of FIG. 4, at any instant in time during which the tabs 61, 63 are being operated, one of the tabs 61, 63 will have a fixed relationship with the base 50 while the other tab is moved relative to the base 50. As the moving tab bends its associated wing, resistance to further bending increases and that tab becomes stationary as the other tab begins to move. Of course, in the two tab embodiment of FIGS. 1–4, this independent movement of the tabs 61, 63 happens relatively fast so that it appears that both of the tabs 61, 63 are moving simultaneously.

The extension tube 16 of the embodiment of FIG. 3 is attached to the sleeve 12 by a coupling 85 including first and second components 87 and 90 respectively which have a snap fit relationship. The components 87, 90 can be formed from a plastic material with the component 87 being molded into the elastomeric material of the sleeve 12. The desired fixed relationship between the extension tube 16 and sleeve 12 is achieved by snapping the component 90 onto the component 87 to complete the coupling 85.

As illustrated in FIGS. 6 and 7, the component 90 can be formed in the shape of an octagon 92 in a male configuration, while the component 87 can be formed in the shape of the octagon 92 with a female configuration.

Many of the structural elements associated with the embodiments of FIGS. 8, 9 and 10 are similar to those previously discussed and accordingly will be assigned the same reference numerals followed by the lower case letter "c". Thus in FIG. 8, a collar 14c includes a base 50c and a pair of wings 52c and 54c. In this case, however, the collar 14c is provided with a pair of diametrically opposed suture flanges 96 and 98. These flanges 96, 98 extend radially in a fixed relationship with the base 50c and a non-perpendicular relationship with an axis 18c. Each of the flanges 96, 98 is provided with a plurality of suture slots 99 which facilitate attachment of a suture between an associated one of the flanges 96, 98 and the abdominal wall 32. These sutures aid in maintaining the desired fixed relationship between the clamp 10c and the abdominal wall 32.

The clamp 10c also includes a sleeve 12c and an integral extension tube 16c. This combination of sleeve 12c and tube 16c is formed from the same elastomeric material. In the illustrated embodiment, the outer surface 17c of the tube 16c is formed in the shape of a cone rather than the cylinder of the FIG. 1 embodiment. The projections 36c extending outwardly from the surface 17c are formed as a plurality of concentric, axially spaced, discrete annuli 101, 103 and 105.

In the embodiment of FIG. 11 a clamp 10d includes a sleeve (similar to the sleeve 12 but not shown) and collar 14d similar to that previously discussed. In this embodiment however, an extension tube 16d is formed with a generally cylindrical configuration. Of particular interest in this embodiment is a projection 36d in the form of a balloon 110 which extends along an outer surface 17d of the tube 16d. This balloon 110 is inflatable through a conduit 112 to expand the diameter of the balloon 110. When operatively disposed, the clamp 10d is positioned within the puncture site 34 (FIG. 2) and the balloon 110 is inflated to anchor the tube 16d within the wall 32. The inflated balloon 110 also creates a pressure against the puncture site 34 where it functions as a tamponade to inhibit bleeding.

Figure 12:
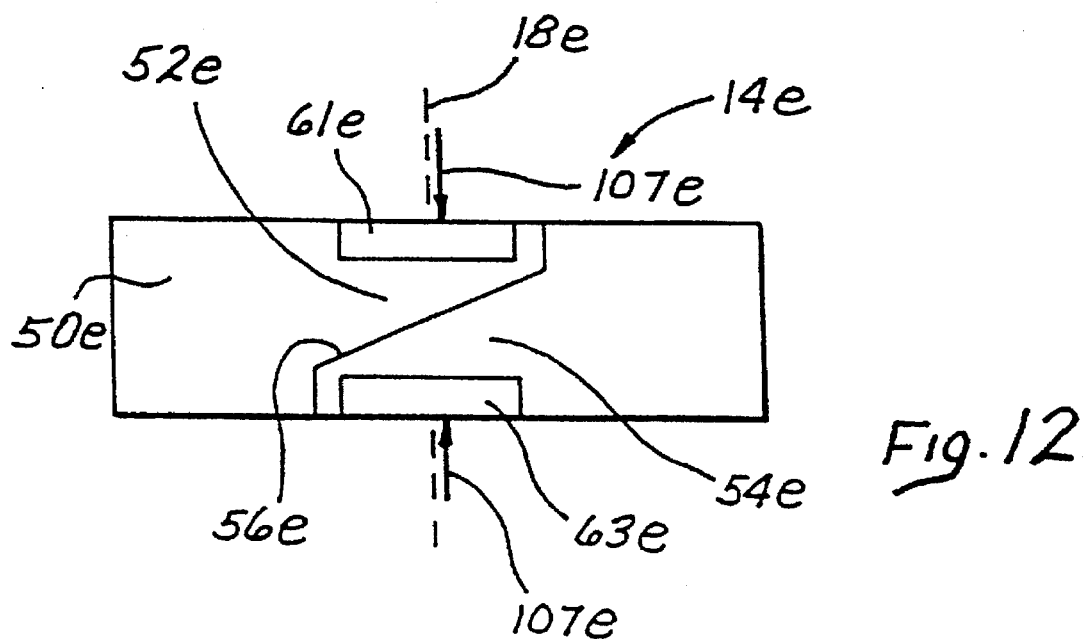
FIG. 12 is a side elevation view similar to FIG. 4c of still a further embodiment of the invention.

A further embodiment of the constriction member or adjustable collar 14e is illustrated in FIG. 12. This embodiment includes a base 50e and tabs 61e and 63e which are movable relative to each other. As in previous embodiments, the tabs 61e and 63e are separated by a slot 56e which in this embodiment is transverse to an axis 18e of the clamp.

In this embodiment, the tab 61e and 63e are movable toward each other along a path of movement illustrated by the arrows 107e. Whereas this path of movement is in a plane transverse or perpendicular to the axis 18 in the embodiment of FIG. 4b, the plane is generally parallel to the axis 18e in the FIG. 12 embodiment. As these tabs 61e and 63e are moved toward each other, the associated wings 52e and 54e slide against each other along the slot 56e in a camming action which tends to separate the wings 52e and 54e and thereby enlarge the diameter of the collar 14e.

From the foregoing discussion of the preferred embodiments, it will be apparent that this concept can be significantly modified while maintaining the advantages associated with the concept. For example, the invention can be embodied with one or more wings 52, 54, each associated with a respective tab 61, 63. Other means for biasing the collar 14 to its constricted state will also be apparent. Certainly the tabs 61 and 63 can be disposed in a variety of positions to facilitate their closure along a path of movement which may be either transverse or parallel to the axis 18.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A combination for accessing a body cavity through a body wall, comprising:

a trocar including a cannula having an axis and an outer surface, the cannula being adapted to extend through the body wall to provide a working channel into the body cavity;

a laparoscopic clamp operable to releasibly engage the cannula of the trocar and maneuverable to an operative position relative to the body wall in order to provide the cannula and the body wall with a generally fixed relationship;

an elastomeric sleeve included in the laparoscopic clamp and being actuable between a first position wherein the sleeve has a generally fixed relationship with a cannula and a second position wherein the sleeve has a sliding relationship with the cannula; and an actuation collar included in the laparoscopic clamp and operable by only one hand of a user to actuate the sleeve between the first position and the second position in order to adjust the position of the clamp relative to the trocar.

2. The combination recited in claim 1 wherein the actuation collar includes:

means for biasing the sleeve to the first position wherein the sleeve has a generally fixed relationship with the cannula.

3. The combination recited in claim 1 wherein the actuation collar includes:

a circumferential constriction member operable by only two fingers of the user's hand to simultaneously actuate the sleeve between the first position and the second position and to maneuver the clamp relative to the body wall.

4. The combination recited in claim 1 wherein the laparoscopic clamp further comprises:

a tube extending axially of the sleeve and having an outer surface for engaging the body wall; and a protrusion on the outer surface of the tube which enhances the fixed relationship between the clamp and the body wall.

5. The combination recited in claim 4 wherein the outer surface of the tube is cylindrical and the protrusion is in the form of a helix.

6. The combination recited in claim 4 wherein the outer surface of the tube is conical and the protrusion is in the form of at least one annulus.

7. The combination recited in claim 4 wherein the clamp further comprises:

a coupler disposed between the tube and the sleeve, the coupler comprising a female portion attached to one of the sleeve and the tube and a male portion attached to the other of the sleeve and the tube; and the male portion being snap fit into the female portion in order to maintain the tube and the sleeve in a generally fixed relationship.

8. A surgical clamp having an axis and being adapted to releasibly engage the outer surface of a cylindrical instrument, comprising:

an elastomeric sleeve having an outer surface and an inner surface, the sleeve being sized and configured to frictionally engage the outer surface of the instrument;

a constriction member forming a ring around the sleeve, the constriction member being operable between a first position wherein the ring is provided with a first diameter and a second position wherein the ring is provided with a second diameter larger than the first diameter;

a pair of tabs attached to the constriction member and being movable relative to each other to operate the constriction member between the first position and second position.

9. The surgical clamp recited in claim 8 wherein at least one of the tabs has a generally fixed relationship with the constriction member during movement of the tabs relative to each other.

10. The surgical clamp recited in claim 8 wherein the tabs are positioned with respect to the sleeve so that the relative movement of the tabs is along a path of movement which extends along a plane transverse to the axis of the sleeve.

11. The surgical clamp recited in claim 8 wherein the constriction member further comprises:

a base;

at least one wing connected to the base and forming the ring with the base, the wing being movable radially of the axis to operate the constriction member between the first position and the second position; and only one of the tabs being attached to the one wing.

12. The surgical clamp recited in claim 11 wherein the one wing is a first wing and the constriction member further comprises:

a second wing connected to the base and forming the ring with the base and the first wing; and the other of the tabs being attached to the second wing.

13. The surgical clamp recited in claim 12 wherein the ring has the configuration of a cylinder with a particular length along the axis of the clamp, and each of the tabs has an axial dimension at least as long as the particular length of the cylinder.

14. The surgical clamp recited in claim 8 further comprising:

a tube extending axially of the constriction member and having an outer surface for engaging the body walls; and a protrusion extending outwardly of the outer surface of the tube for enhancing the first relationship between the tube and the body wall.

15. The surgical clamp recited in claim 8 wherein the clamp is operable using only one hand by squeezing the tabs relative to each other between the thumb and finger of the user's hand.

16. The surgical clamp recited in claim 8 further comprising: serrations disposed on the tabs to enhance a frictional relationship between the tabs and the hand of the user.

17. The surgical clamp recited in claim 8 wherein:

the tabs are moveable in a particular plane; and
the particular plane is transverse to the axis of the clamp.

18. The surgical clamp recited in claim 8 wherein:

the tabs are moveable in a particular plane; and
the particular plane is generally parallel to the axis of the clamp.

19. The surgical clamp recited in claim 14 wherein the protrusion includes a helix.

20. The surgical clamp recited in claim 14 wherein the protrusion includes a plurality of annuli.

21. The surgical clamp recited in claim 14 wherein the protrusion includes an inflatable balloon.

\* \* \* \* \*